US008779191B2

(12) United States Patent
Bauer et al.

(10) Patent No.: US 8,779,191 B2
(45) Date of Patent: Jul. 15, 2014

(54) METHODS AND COMPOSITIONS FOR PREPARING LISDEXAMFETAMINE AND SALTS THEREOF

(75) Inventors: Michael J. Bauer, Charles City, IA (US); Gary Richard Callen, Charles City, IA (US); Judi Christine Humphrey, Charles City, IA (US); Todd Jeffrey Johnson, Olds, IA (US); Matthew Wendell Schiesher, Charles City, IA (US)

(73) Assignee: Cambrex Charles City, Inc., Charles City, IA (US)

( * ) Notice: Subject to any disclaimer, the term of this patent is extended or adjusted under 35 U.S.C. 154(b) by 236 days.

(21) Appl. No.: 12/973,453

(22) Filed: Dec. 20, 2010

(65) Prior Publication Data

US 2012/0157706 A1 Jun. 21, 2012

(51) Int. Cl.
*C07C 229/00* (2006.01)
*C07C 233/00* (2006.01)

(52) U.S. Cl.
USPC .......................................... 562/562; 564/193

(58) Field of Classification Search
None
See application file for complete search history.

(56) References Cited

U.S. PATENT DOCUMENTS

| | | | |
|---|---|---|---|
| 6,384,020 B1 | 5/2002 | Flanner et al. | |
| 6,399,828 B1 | 6/2002 | Boswell et al. | |
| 7,105,486 B2 | 9/2006 | Mickle et al. | |
| 7,223,735 B2 | 5/2007 | Mickle et al. | |
| 7,705,184 B2 | 4/2010 | Buenger et al. | |
| 2005/0038121 A1* | 2/2005 | Mickle et al. | 514/563 |
| 2005/0208604 A1 | 9/2005 | Zheng et al. | |
| 2007/0042955 A1 | 2/2007 | Mickle et al. | |
| 2008/0086016 A1 | 4/2008 | Mickle et al. | |
| 2011/0196173 A1* | 8/2011 | Meudt et al. | 564/194 |
| 2012/0190880 A1 | 7/2012 | Jass et al. | |

FOREIGN PATENT DOCUMENTS

| | | | |
|---|---|---|---|
| DE | 13785 | | 9/1957 |
| DE | 1493824 | * | 5/1969 |
| WO | WO-2008/073918 | | 6/2008 |
| WO | WO-2008/098151 | | 8/2008 |
| WO | WO-2008/103538 | | 8/2008 |

OTHER PUBLICATIONS

"Benzyl Chloroformate" in Handbook of Reagents for Organic Synthesis—Activating Agents and Protecting Groups; Pearson et al., eds., 1999 John Wiley & Sons, pp. 46-50.*
Smith and March. Advanced Organic Chemistry 6th ed. (501-502).*
Database Caplus Chemical Abstracts Service, Columbus, Ohio, US; Database Accession No. 1966:19805, Abstract NL 6414901, Jul. 28, 1965.*
Curran, William V. and Boothe, James H. (1978) "The synthesis of deoxynegamycin and some related compounds," *Journal of Antibiotics*, 31(9), pp. 914-918. (abstract only).
International Preliminary Report on Patentability of the International Searching Authority of International Patent Application No. PCT/US2010/039174, issued on Dec. 20, 2011 (9 pages).
International Search Report for International Application No. PCT/US2010/39174, filed Jun. 18, 2010, date of mailing Nov. 15, 2010.
Jass, Paul A. et al. (2003) "Use of *N*-trifluoroacetyl-protected amino acid chlorides in peptide coupling reactions with virtually complete preservation of stereochemistry," *Tetrahedron*, 59(45), pp. 9019-9029. (abstract only).
Mikhaleva et al. (1980) "Study of the synthesis of α-bungarotoxin. I. Synthesis of a protected heptatriacontapeptide with a sequence (38-74) of α-bungarotoxin," *Bioorganicheskaya Khimiya*, 6(7), pp. 982-1007. (abstract only).
Muller, Horst K. (1956) "Partial asymmetric syntheses of ephedrine derivatives influenced by side-chains and nuclear substituents," *Justus Liebigs Annalen der Chemie*, vol. 599, pp. 211-221. (abstract only).
Taguchi, Tanezo and Kojima, Masaharu (1955) "Stereochemistry. IV. Alkanolamines. 4. Regular dl-2,5-diphenyl-4-methyloxazoline: The formation and action of methyl tosylate," *Pharmaceutical Bulletin*, vol. 3, pp. 4-7. (abstract only).

* cited by examiner

*Primary Examiner* — Karl J Puttlitz
(74) *Attorney, Agent, or Firm* — Banner & Witcoff, Ltd.

(57) ABSTRACT

The invention provides methods and compositions for preparing lisdexamfetamine and salts thereof. More particularly, the invention provides, for example, methods of preparing lisdexamfetamine from D-amphetamine.

15 Claims, No Drawings

METHODS AND COMPOSITIONS FOR PREPARING LISDEXAMFETAMINE AND SALTS THEREOF

FIELD OF THE INVENTION

The invention provides methods and compositions for preparing the pharmaceutical agent lisdexamfetamine and salts thereof. More particularly, the invention provides, for example, methods of preparing lisdexamfetamine from D-amphetamine.

BACKGROUND OF THE INVENTION

Lisdexamfetamine dimesylate is approved and marketed in the United States for the treatment of attention-deficit hyperactivity disorder in pediatric patients. The active compound lisdexamfetamine contains D-amphetamine covalently linked to the essential amino acid L-lysine. Controlled release of D-amphetamine, a psychostimulant, occurs following administration of lisdexamfetamine to a patient. The controlled release has been reported to occur through hydrolysis of the amide bond linking D-amphetamine and L-lysine.

A procedure for making lisdexamfetamine hydrochloride is described in U.S. Pat. No. 7,223,735 to Mickle et al. (hereinafter Mickle). The procedure involves reacting D-amphetamine with (S)-2,5-dioxopyrrolidin-1-yl 2,6-bis(tert-butoxycarbonylamino)hexanoate to form a lysine-amphetamine intermediate bearing tert-butylcarbamate protecting groups. This intermediate is treated with hydrochloric acid to remove the tert-butylcarbamate protecting groups and provide lisdexamfetamine as its hydrochloride salt. However, this procedure suffers several drawbacks that are problematic when carrying out large scale reactions, such as manufacturing scale, to prepare lisdexamfetamine.

The need exists for new methods and compositions for preparing lisdexamfetamine and salts thereof, particularly in high enantiomeric purity. The invention addresses this need and has other related advantages.

SUMMARY

The invention provides methods and compositions for preparing lisdexamfetamine and salts thereof. The synthetic method provides numerous advantages that are particularly important to a manufacturing scale synthesis of lisdexamfetamine. One advantage is that the process provides a crystalline solid synthetic intermediate that is easy to purify by crystallization. Another advantage is that the lisdexamfetamine can be prepared with high purity, such as greater than 99.9% (w/w) purity, even when using low-purity amphetamine. Other advantages of the methods and compositions are described below and will be apparent to the skilled artisan upon reading of the description and examples herein.

Accordingly, one aspect of the invention provides a method of preparing an acyl-amphetamine compound. The method comprises admixing an amphetamine compound of Formula I with a lysine compound of Formula II to provide a lysine-amphetamine compound of Formula III, wherein Formula I is represented by:

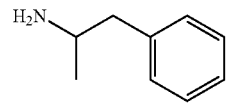

or a salt thereof;
Formula II is represented by:

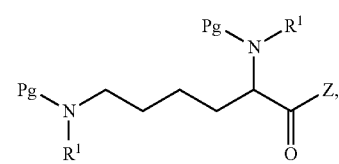

wherein:
R$^1$ represents independently for each occurrence hydrogen or C$_1$-C$_6$ alkyl;
Pg represents independently for each occurrence a protecting group that undergoes deprotection under hydrogenation conditions and contains at least one aromatic ring; and
Z is a leaving group; and
Formula III is represented by:

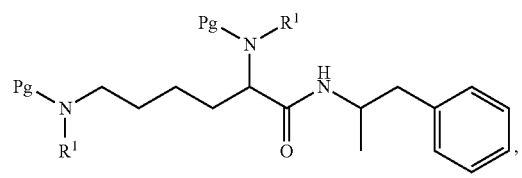

wherein:
R$^1$ represents independently for each occurrence hydrogen or C$_1$-C$_6$ alkyl; and
Pg represents independently for each occurrence a protecting group that undergoes deprotection under hydrogenation conditions and contains at least one aromatic ring.

Another aspect of the invention provides compounds that are valuable intermediates in the synthesis of lisdexamfetamine. In certain embodiments, the invention provides a compound of Formula III:

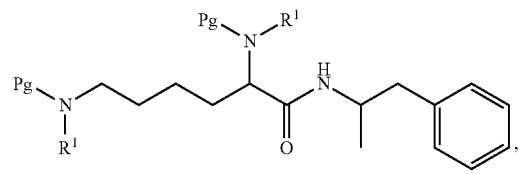

wherein:
Pg represents independently for each occurrence —C(R$^2$)$_2$-aryl or —C(O)OC(R$^2$)$_2$-aryl;
R$^1$ represents independently for each occurrence hydrogen or C$_1$-C$_6$ alkyl; and
R$^2$ represents independently for each occurrence hydrogen or C$_1$-C$_4$ alkyl.

DETAILED DESCRIPTION OF THE INVENTION

The invention provides methods and compositions for preparing lisdexamfetamine and salts thereof. The synthetic methods provide numerous advantages that are particularly important to a manufacturing scale synthesis of lisdexamfetamine. The practice of the invention employs, unless otherwise indicated, conventional techniques of organic chemistry, such as described in "Comprehensive Organic Synthesis" (B. M. Trost & I. Fleming, eds., 1991-1992). Various aspects of the invention are described below.

I. Description of the Overall Synthesis of Lisdexamfetamine and Related Compounds Exemplary methods for preparing lisdexamfetamine (LDX) and related compounds are described below in the synthetic schemes and accompanying description. In particular, the overall synthetic strategy for preparing lisdexamfetamine dimesylate is shown in Scheme 1. This strategy uses L-lysine and D-amphetamine starting materials, both of which are commercially available. The L-lysine is converted to intermediate B for amide coupling with D-amphetamine (C). A variety of protecting groups (Pg) on lysine intermediate A are contemplated to be amenable to the present synthetic strategy. See, for example, Greene, T. W.; Wuts, P. G. M. *Protective Groups in Organic Synthesis*, $2^{nd}$ ed.; Wiley: New York, 1991 for a general description of protecting groups. The protecting groups (Pg) should be capable of undergoing deprotection under hydrogenation conditions, and preferably, contain at least one aromatic group. One particularly preferred protecting group is benzyloxycarbonyl.

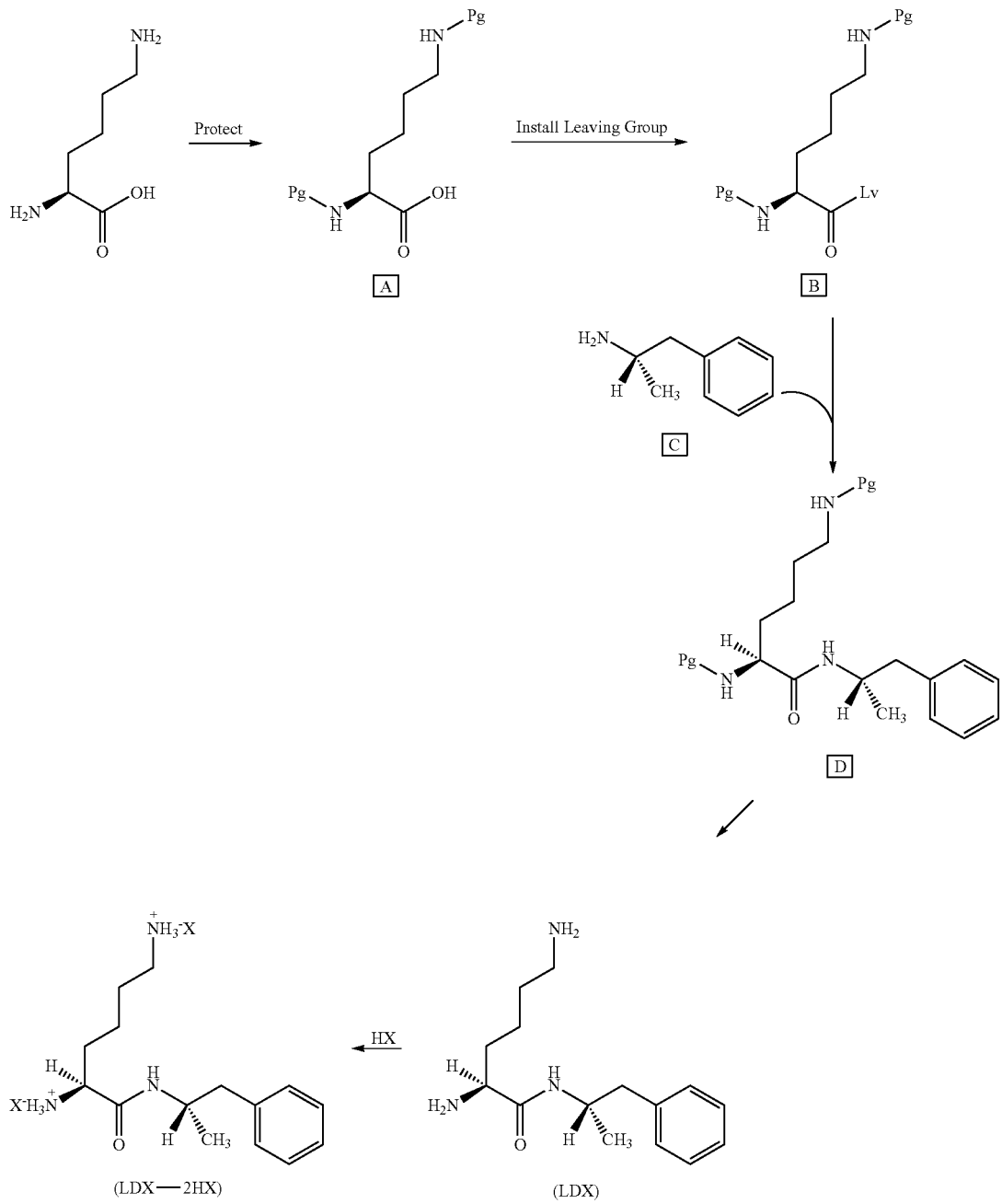

SCHEME 1

Amide coupling of lysine intermediate B and D-amphetamine (C) to provide lysine-amphetamine D can be carried out using a variety of different leaving groups. Particularly preferred leaving groups include chloro and N-hydroxysuccinimidyl. Lysine-amphetamine D is desirably a crystalline solid that can be easily purified by recrystallization. The next phase of the synthetic procedure involves removal of the amino protecting groups from lysine-amphetamine intermediate D. For example, when the protecting groups are benzyloxycarbonyl groups, hydrogenation in the presence of a palladium catalyst (e.g., Pd/C) can be used to remove the protecting groups. Salt forms of LDX can be prepared by reacting LDX with the desired acid. For example, the dimesylate salt of LDX can be prepared by reacting LDX with methanesulfonic acid.

Further advantages of the synthetic process include providing the lisdexamfetamine in high enantiomeric purity and free of toxic impurities, and providing synthetic intermediates that can be used directly in the next reaction step without costly or time-consuming purification of the synthetic intermediate. A synthetic process that provides lisdexamfetamine dimesylate in high enantiomeric purity is important because the therapeutic agent approved for treatment of attention-deficit hyperactivity disorder is a single enantiomer. Accordingly, a manufacturing process to supply the drug must be able to provide lisdexamfetamine dimesylate in high enantiomeric purity.

The procedure illustrated in Scheme 1 achieves high enantiomeric purity through a combination of features. One aspect of the synthesis that contributes to the high enantiomeric purity of the final product is that lysine-amphetamine intermediate D can be a crystalline solid, and it is possible to isolate the desired enantiomer through selective crystallization. Use of starting material (i.e., L-lysine and D-amphetamine) having high enantiomeric purity can enhance the enantiomeric purity of the final product.

Other advantages of the methods and compositions are described below and will be apparent to the skilled artisan upon reading of the description and examples herein. Particular aspects of the synthetic procedure outlined in Scheme 1 are described in more detail below and further illustrated in Schemes 2-5.

Scheme 2 illustrates an exemplary method for preparing LDX-(Cbz)$_2$-NHS. The exemplary procedure involves reacting the protected lysine compound with disuccinimidyl carbonate, which can be added directly to the protected lysine compound or the disuccinimidyl carbonate can be generated in situ from dicyclohexylcarbodiimide and N-hydroxysuccinimide. LDX-(Cbz)$_2$-NHS can also be purchased from commercial sources.

SCHEME 2

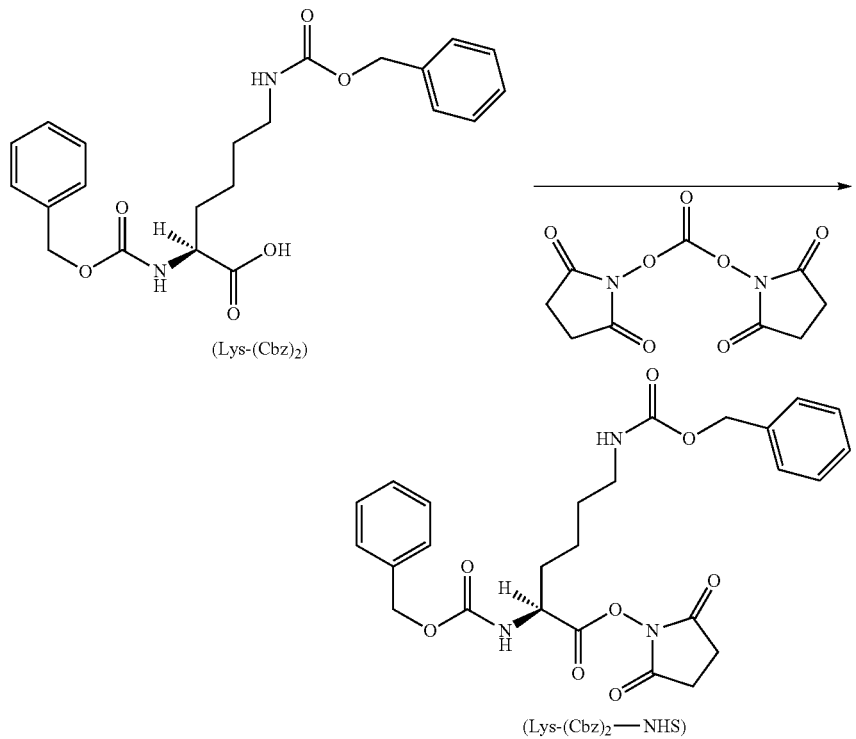

(Lys-(Cbz)$_2$)

(Lys-(Cbz)$_2$—NHS)

Scheme 3 illustrates preparation of Cbz-protected lisdexamfetamine (LDX-(Cbz)$_2$). The procedure involves reacting the protected, activated lysine compound Lys-(Cbz)$_2$-NHS with D-amphetamine to provide amide coupling product LDX-(Cbz)$_2$. Various activated forms of Lys-(Cbz)$_2$ are contemplated to be amenable to amide coupling with D-amphetamine. For example, in place of the N-hydroxysuccinimide ester leaving group, the activated Lys-(Cbz)$_2$ may be an acid chloride or other leaving group known in the art as being amenable to amide coupling conditions. An acid chloride can be prepared from a carboxylic acid using techniques described in the literature, such as reacting the carboxylic acid with Vilsmeier Reagent, thionyl chloride, oxalyl chloride, phosphorous trichloride, or phosphorous pentachloride. Other reagents used to activate a carboxylic acid group for reaction with an amine (e.g., D-amphetamine) include, for example, carbodiimides (such as dicyclohexylcarbodiimide; N,N'-diisopropylcarbodiimide; and 1-ethyl-3-(3-dimethylaminopropyl)carbodiimide), phosphonium reagents (such as benzotriazol-1-yloxytris(dimethylamino)phosphonium hexafluorophosphate), uronium reagents (2-(1H-benzotriazole-1-yl)-1,1,3,3-tetramethyluronium hexafluorophosphate), anhydrous 1-hydroxybenzotriazole, and phosphonic acid anhydrides (such as propane phosphonic acid anhydride, sold under the tradename T3P®).

The LDX-(Cbz)$_2$ is a crystalline solid that can be isolated from the reaction mixture by recrystallization from a mixture of methanol and isopropyl acetate. The LDX-(Cbz)$_2$ material isolated from the reaction mixture can be further purified by recrystallization from methanol to provide highly pure LDX-(Cbz)$_2$. This recrystallization from methanol has provided material that is at least 99.95% pure by HPLC and $^1$H NMR analysis. This recrystallization procedure permits removal of undesired diastereomers of the LDX-(Cbz)$_2$ product shown in Scheme 3, which may have resulted from L-amphetamine impurities in the D-amphetamine starting material. Moreover, the recrystallization purification procedure permits use of D-amphetamine containing small quantities of L-amphetamine since LDX-(Cbz)$_2$ product resulting from the L-amphetamine impurities in the starting material can be removed by the crystallization purification procedure. Furthermore, when the leaving group is N-hydroxysuccinimide, recrystallization of the LDX-(Cbz)$_2$ reaction product from methanol reduces the amount of N-hydroxysuccinimide reaction by-product from the LDX-(Cbz)$_2$ product.

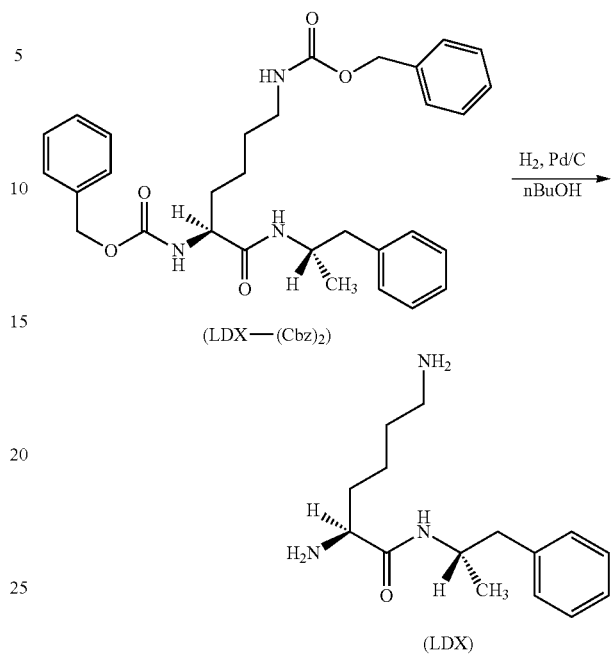

SCHEME 4

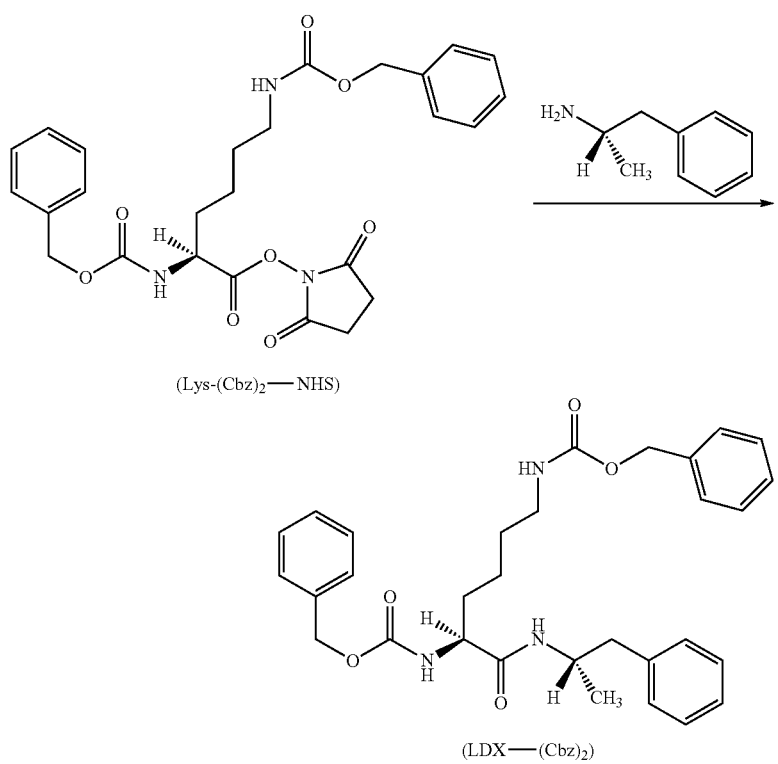

SCHEME 3

Scheme 4 illustrates preparation of lisdexamfetamine (LDX). The procedure involves removing the protecting groups from LDX-(Cbz)$_2$ under hydrogenation conditions, such as hydrogen gas in the presence of a palladium catalyst.

Scheme 5 illustrates preparation of lisdexamfetamine dimesylate (LDX-2MSA). The procedure involves reacting LDX with methanesulfonic acid. It is contemplated that other acid salts of LDX can be prepared using a similar procedure by substituting another acid (e.g., HCl, HBr, and the like) for methanesulfonic acid.

SCHEME 5

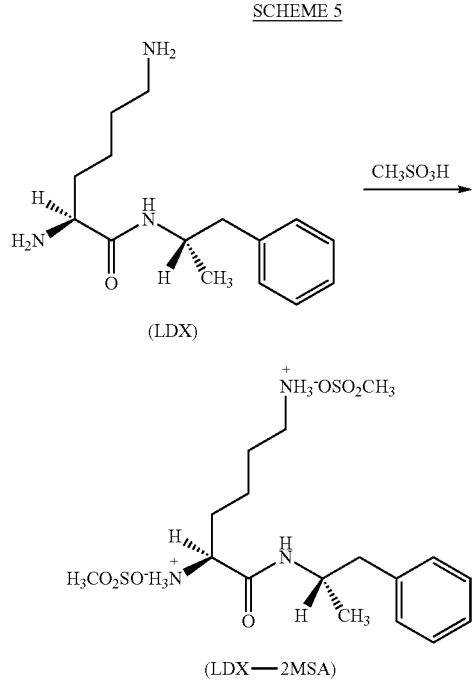

(LDX)

(LDX—2MSA)

II. Description of Preferred Aspects of the Synthesis of Lisdexamfetamine and Related Compounds One aspect of the invention provides a method of preparing a lysine-amphetamine compound, comprising admixing an amphetamine compound of Formula I with a lysine compound of Formula II to provide a lysine-amphetamine compound of Formula III, wherein Formula I is represented by:

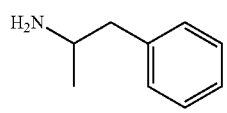

or a salt thereof;

Formula II is represented by:

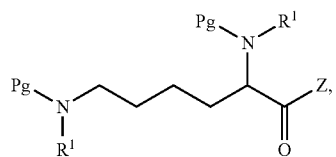

wherein:

$R^1$ represents independently for each occurrence hydrogen or $C_1$-$C_6$ alkyl;

Pg represents independently for each occurrence a protecting group that undergoes deprotection under hydrogenation conditions and contains at least one aromatic ring; and Z is a leaving group; and Formula III is represented by:

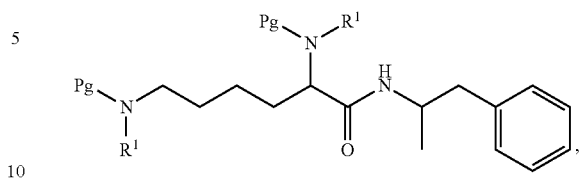

wherein:

$R^1$ represents independently for each occurrence hydrogen or $C_1$-$C_6$ alkyl; and Pg represents independently for each occurrence a protecting group that undergoes deprotection under hydrogenation conditions and contains at least one aromatic ring.

Protecting groups that undergo deprotection under hydrogenation conditions are known in the art. See, for example, Greene, T. W.; Wuts, P. G. M. *Protective Groups in Organic Synthesis*, $2^{nd}$ ed.; Wiley: New York, 1991. In certain embodiments, Pg is

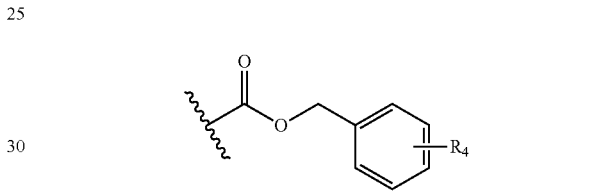

wherein $R_4$ represents independently for each occurrence hydrogen, $C_1$-$C_6$ alkyl, halogen, $C_1$-$C_6$ haloalkyl, or $C_1$-$C_6$ alkoxy. In certain other embodiments, Pg is —C(O)OCH$_2$—Ar, wherein Ar is phenyl optionally substituted with one or more substituents independently selected from the group consisting of halogen, nitro, —OC(O)-alkyl, —OC(O)-aryl, boronate ester, alkoxy, and alkyl. In certain other embodiments, Pg is one of the following:

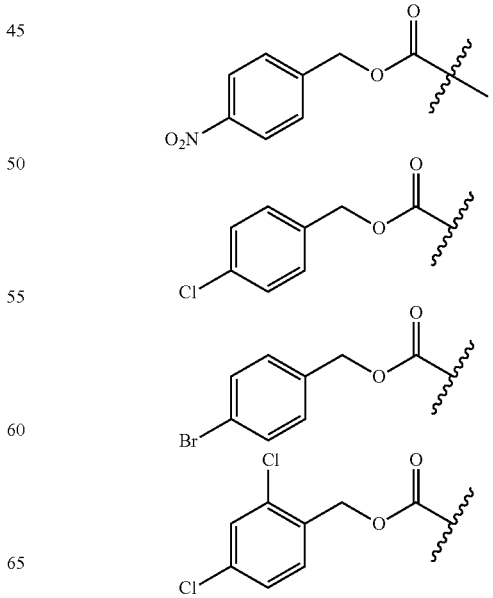

-continued

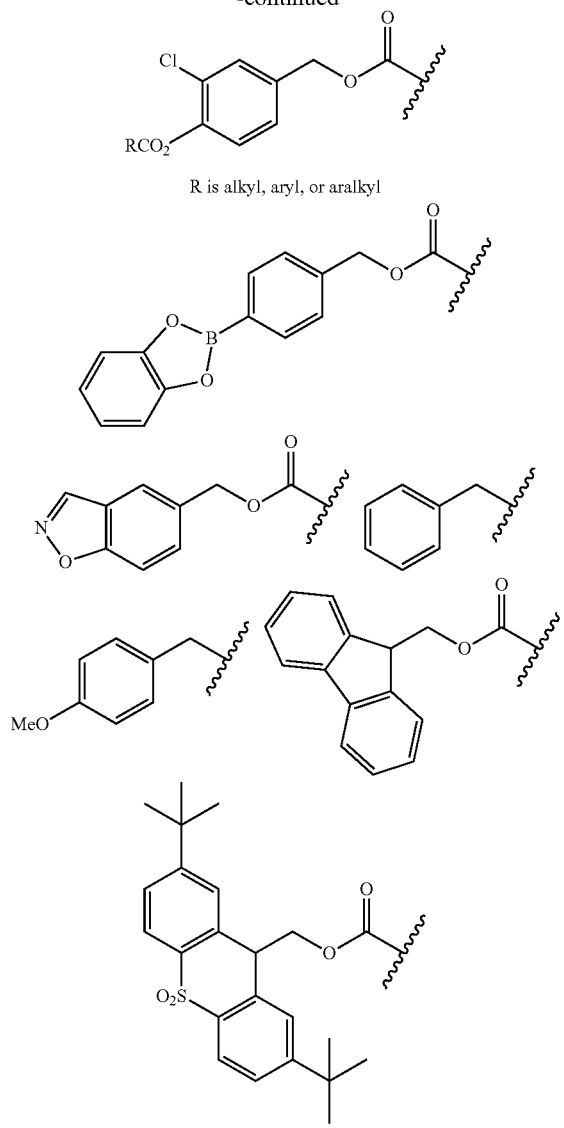

R is alkyl, aryl, or aralkyl

In certain other embodiments, Pg is —C(R$^2$)$_2$-aryl or —C(O)OC(R$^2$)$_2$-aryl, wherein R$^2$ represents independently for each occurrence hydrogen or C$_1$-C$_4$ alkyl. In certain other embodiments, Pg is —C(O)OCH$_2$-phenyl, wherein said phenyl is optionally substituted with 1, 2, or 3 substituents independently selected from the group consisting of halogen, C$_1$-C$_6$ alkyl, and C$_1$-C$_6$ alkoxy. In certain other embodiments, Pg is —C(O)OCH$_2$-phenyl.

In certain embodiments, Z is Cl, Br, I,

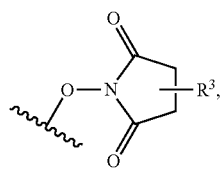

—O—C(=N(cycloalkyl))(N(H)(cycloalkyl)), or —O—C(=N(alkyl optionally substituted with a dialkylamino group))(N(H)(alkyl optionally substituted with a dialkylamino group)); wherein R$^3$ is hydrogen or C$_1$-C$_6$ alkyl. In certain other embodiments, Z is Cl.

In certain embodiments, R$_1$ is hydrogen.
In certain embodiments, Formula I is

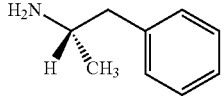

having a purity of at least 90% (w/w), Formula II is

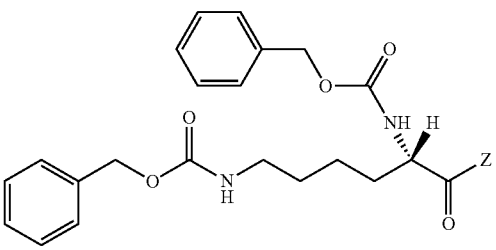

wherein Z is a leaving group, and Formula III is

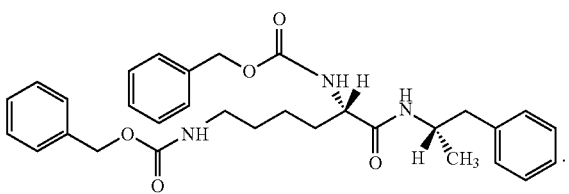 [SMILES: C[C@@H](Cc1ccccc1)NC(=O)[C@H](CCCCNC(=O)OCc1ccccc1)NC(=O)OCc1ccccc1]

In certain embodiments, Z is Cl or

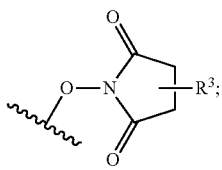

wherein R$^3$ is hydrogen or C$_1$-C$_6$ alkyl.

In certain embodiments, Formula I has a purity of at least 95% (w/w), 97% (w/w), 98% (w/w), or 99% (w/w).

In certain embodiments, the method further comprises crystallizing said lysine-amphetamine compound of Formula III to provide a purified lysine-amphetamine compound of Formula III. The crystallizing may be performed using a mixture comprising at least one of a C$_1$-C$_4$ aliphatic alcohol, C$_1$-C$_4$ aliphatic carboxylic acid, aliphatic tertiary amine, or water, to provide the purified lysine-amphetamine compound of Formula III.

In certain embodiments, the method further comprises crystallizing said lysine-amphetamine compound of Formula III from a mixture comprising (i) at least one of a C$_1$-C$_4$ aliphatic alcohol, C$_1$-C$_4$ aliphatic carboxylic acid, aliphatic tertiary amine, or water, and (ii) (C$_1$-C$_4$ alkyl)—CO$_2$—(C$_1$-C$_4$ alkyl), to provide the purified lysine-amphetamine compound of Formula III. In certain other embodiments, the method further comprises crystallizing said lysine-amphetamine compound of Formula III from a mixture comprising a $C_1$-$C_4$ aliphatic alcohol and ($C_1$-$C_4$ alkyl)—$CO_2$—($C_1$-$C_4$ alkyl), to provide the purified lysine-amphetamine compound of Formula III. In certain embodiments, the method further comprises crystallizing said lysine-amphetamine compound of Formula III from a mixture comprising methanol and isopropyl acetate to provide a purified lysine-amphetamine compound of Formula III. In certain embodiments, the method further comprises crystallizing said lysine-amphetamine compound of Formula III from a mixture comprising (i) at least 20% (v/v) methanol, and (ii) at least 20% (v/v) isopropyl acetate, to provide a purified lysine-amphetamine compound of Formula III. In certain embodiments, the method further comprises crystallizing said lysine-amphetamine compound of Formula III from a mixture comprising (i) at least 40% (v/v) methanol, and (ii) at least 40% (v/v) isopropyl acetate, to provide a purified lysine-amphetamine compound of Formula III.

In certain embodiments, the crystallizing step comprises first heating to a temperature greater than 55° C. a purification mixture formed by addition of methanol to the reaction mixture, and then cooling the purification mixture to a temperature in the range of 40° C. to 55° C. In certain embodiments, the crystallizing further comprises holding the purification mixture at a temperature in the range of 40° C. to 55° C. for 8 hours to 24 hours. In certain embodiments, the crystallizing further comprises holding the purification mixture a temperature in the range of 40° C. to 55° C. for 8 hours to 24 hours, and then cooling the purification mixture at a rate of 5° C. to 10° C. per hour until the purification mixture reaches a temperature in the range of 15° C. to 25° C. In certain embodiments, the purification mixture comprises lysine-amphetamine compound of Formula III in about 5% (w/w) to about 20% (w.w), or about 7% (w/w) to about 15% (w/w).

In certain embodiments, the purified lysine-amphetamine compound of Formula III has a purity of at least 99% (w/w). In certain embodiments, the purified lysine-amphetamine compound of Formula III has a purity of at least 99.5% (w/w) or 99.9% (w/w). In certain embodiments, the purified lysine-amphetamine compound of Formula III contains less than 1% (w/w) N-hydroxysuccinimide, or less than 0.6% (w/w) N-hydroxysuccinimide.

In certain embodiments, the method further comprises re-crystallizing said purified lysine-amphetamine compound of Formula III from a mixture comprising at least one of a $C_1$-$C_4$ aliphatic alcohol, $C_1$-$C_4$ aliphatic carboxylic acid, aliphatic tertiary amine, or water, to provide a high-purity lysine-amphetamine compound of Formula III. In certain other embodiments, the method further comprises re-crystallizing said purified lysine-amphetamine compound of Formula III from a mixture comprising a $C_1$-$C_4$ aliphatic alcohol, to provide a high-purity lysine-amphetamine compound of Formula III. In certain other embodiments, the method further comprises re-crystallizing said purified lysine-amphetamine compound of Formula III from methanol, to provide a high-purity lysine-amphetamine compound of Formula III.

In certain embodiments, the re-crystallizing step comprises mixing said purified lysine-amphetamine compound of Formula III with methanol to form a re-purification mixture, then heating said re-purification mixture to a temperature greater than 55° C., and then cooling the purification mixture to a temperature in the range of 40° C. to 55° C. In certain embodiments, the re-crystallizing further comprises holding the re-purification mixture at a temperature in the range of 40° C. to 55° C. for 8 hours to 24 hours. In certain embodiments, the re-crystallizing further comprises holding the re-purification mixture a temperature in the range of 40° C. to 55° C. for 8 hours to 24 hours, and then cooling the re-purification mixture at a rate of 5° C. to 10° C. per hour until the re-purification mixture reaches a temperature in the range of 15° C. to 25° C. In certain embodiments, the re-purification mixture comprises purified lysine-amphetamine compound of Formula III in about 5% (w/w) to about 30% (w.w), or about 10% (w/w) to about 30% (w/w), or about 15% (w/w) to about 25% (w/w).

In certain embodiments, the high-purity lysine-amphetamine compound of Formula III has a purity of at least 99.9% (w/w). In certain embodiments, the high-purity lysine-amphetamine compound of Formula III has a purity of at least 99.95% (w/w) or 99.99% (w/w). In certain embodiments, the high-purity lysine-amphetamine compound of Formula III contains less than 0.1% (w/w) N-hydroxysuccinimide, or less than 0.5% (w/w) N-hydroxysuccinimide.

In certain embodiments, the method provides the purified lysine-amphetamine compound of Formula III at a purity of at least 99% (w/w), when starting with a mixture of D-amphetamine and L-amphetamine having an enantiomeric ratio of less than 99:1 (D-amphetamine to L-amphetamine). In certain embodiments, the method provides the purified lysine-amphetamine compound of Formula III at a purity of at least 99.4% (w/w), when starting with a mixture of D-amphetamine and L-amphetamine having an enantiomeric ratio of less than 99:1 (D-amphetamine to L-amphetamine).

In certain embodiments, the high-purity lysine-amphetamine compound of Formula III has a purity of at least 99.9% (w/w), when starting with a mixture of D-amphetamine and L-amphetamine having an enantiomeric ratio of less than 99:1 (D-amphetamine to L-amphetamine). In certain embodiments, the high-purity lysine-amphetamine compound of Formula III has a purity of at least 99.95% (w/w), when starting with a mixture of D-amphetamine and L-amphetamine having an enantiomeric ratio of less than 99:1 (D-amphetamine to L-amphetamine).

In certain embodiments, the method further comprises admixing said lysine-amphetamine compound of Formula III, a hydrogenation catalyst, and a hydrogen source to provide a lysine-amphetamine compound of Formula IV:

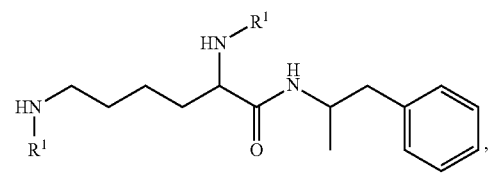

wherein $R^1$ is hydrogen or $C_1$-$C_6$ alkyl.

In certain embodiments, the hydrogenation catalyst comprises palladium. In certain embodiments, the hydrogenation catalyst comprises palladium on carbon, and the hydrogen source is hydrogen gas or ammonium formate.

In certain embodiments, Formula I is

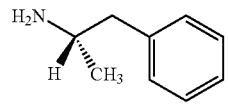

having a purity of at least 90% (w/w), Formula II is

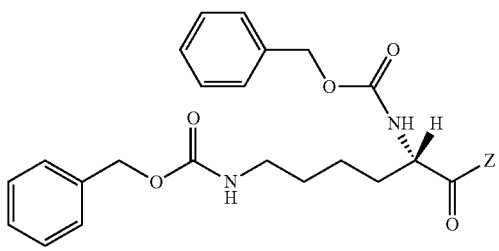

wherein Z is a leaving group, Formula III is

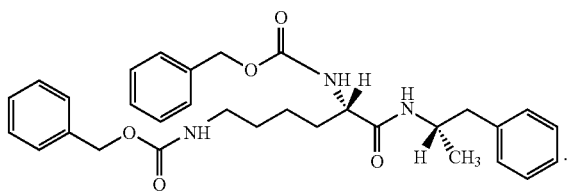 [SMILES: C[C@@H](Cc1ccccc1)NC(=O)[C@H](CCCCNC(=O)OCc1ccccc1)NC(=O)OCc1ccccc1]

and Formula IV is

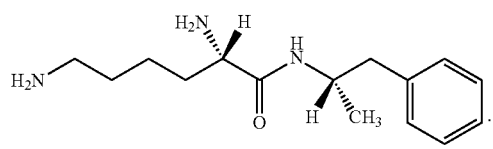 [SMILES: C[C@@H](Cc1ccccc1)NC(=O)[C@@H](N)CCCCN]

In certain embodiments, Z is Cl or

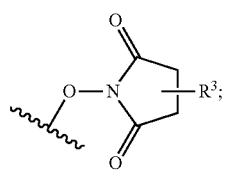

wherein $R^3$ is hydrogen or $C_1$-$C_6$ alkyl.

In certain embodiments, the method further comprises admixing said lysine-amphetamine compound of Formula IV and an acid to provide an acid salt of said lysine-amphetamine compound of Formula IV. In certain embodiments, the acid is methanesulfonic acid. In certain embodiments, the acid is methanesulfonic acid, hydrochloric acid, or hydrobromic acid; and the acid salt of said lysine-amphetamine compound of Formula IV is represented by

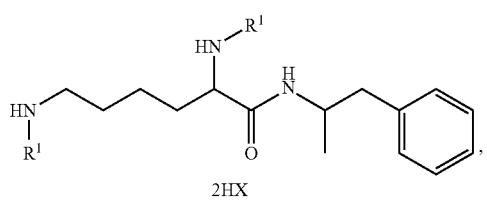

wherein $R^1$ is hydrogen or $C_1$-$C_6$ alkyl; and X is $CH_3SO_2$, Cl, or Br.

In certain embodiments, the acid is methanesulfonic acid, the lysine-amphetamine compound of Formula IV is represented by

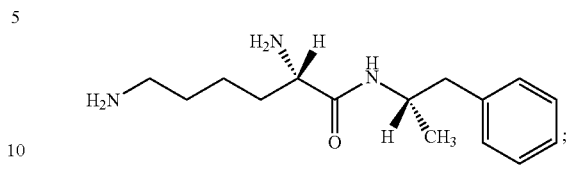

and the acid salt of said lysine-amphetamine compound of Formula IV is represented by:

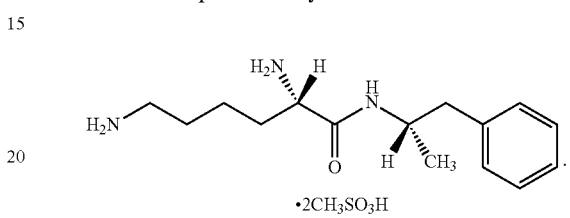

In certain embodiments, the method further comprises admixing a lysine compound of Formula V with a carboxylic acid-activating agent to provide a lysine compound of Formula II; wherein the lysine compound of Formula V is represented by

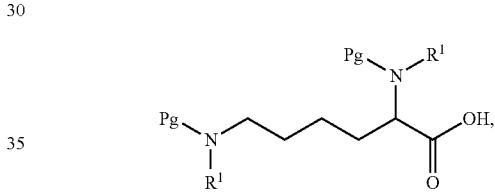

wherein $R^1$ is hydrogen or $C_1$-$C_6$ alkyl, and Pg represents independently for each occurrence a protecting group that undergoes deprotection under hydrogenation conditions and contains at least one aromatic ring. In certain embodiments, Pg is —$C(R^2)_2$-aryl or —$C(O)OC(R^2)_2$-aryl, wherein $R^2$ represents independently for each occurrence hydrogen or $C_1$-$C_4$ alkyl. In certain embodiments, Pg is —$C(O)OCH_2$-phenyl, wherein said phenyl is optionally substituted with 1, 2, or 3 substituents independently selected from the group consisting of halogen, $C_1$-$C_6$ alkyl, and $C_1$-$C_6$ alkoxy. In certain embodiments, Pg is —$C(O)OCH_2$-phenyl.

In certain embodiments, the carboxylic acid-activating agent is Vilsmeier Reagent, thionyl chloride, oxalyl chloride, phosphorous trichloride, or phosphorous pentachloride, a carbodiimide compound (such as dicyclohexylcarbodiimide; N,N'-diisopropylcarbodiimide; and 1-ethyl-3-(3-dimethylaminopropyl)carbodiimide), a phosphonium reagent (such as benzotriazol-1-yloxytris(dimethylamino)phosphonium hexafluorophosphate), a uronium reagent (such as 2-(1H-benzotriazole-1-yl)-1,1,3,3-tetramethyluronium hexafluorophosphate), anhydrous 1-hydroxybenzotriazole, or a phosphonic acid anhydride reagent (such as propane phosphonic acid anhydride, sold under the tradename T3P®).

In certain embodiments, the method relates to any one or more of the above methods, wherein the method(s) are carried out on manufacturing scale. In certain embodiments, the method relates to any one or more of the above methods, wherein the method(s) are carried out at a temperature in the range of about −20° C. to about 60° C. In certain embodiments, the method relates to any one or more of the above methods, wherein the method(s) are carried out at a temperature in the range of about 0° C. to about 35° C., or a range of about 10° C. to about 20° C. In certain embodiments, the method relates to any one or more of the above methods, wherein the method(s) are carried out using a solvent system that is amenable to operation in a stainless steel reaction vessel.

In certain embodiments, the method relates to any one or more of the above methods, wherein the method(s) provide the product with a stereoisomeric purity of greater than 90% enantiomeric excess, greater than 95% enantiomeric excess, greater than 98% enantiomeric excess, or greater than 99% enantiomeric excess. In certain embodiments, the method relates to any one or more of the above methods, wherein the method(s) provide the product with a stereoisomeric purity of greater than 90% diastereomeric excess, greater than 95% diastereomeric excess, greater than 98% diastereomeric excess, or greater than 99% diastereomeric excess.

III. Brief Description of Preferred Synthetic Intermediates in the Synthesis of Lisdexamfetamine and Related Compounds One aspect of the invention provides compounds that are valuable intermediates in the synthesis of lisdexamfetamine. Compounds contemplated to be valuable in the synthesis of lisdexamfetamine are described throughout this disclosure (including the examples) by reference to generic chemical structures and specific compounds, or salts thereof. In certain preferred embodiments, the invention provides a synthetic intermediate compound represented by Formula III, wherein Formula III is represented by:

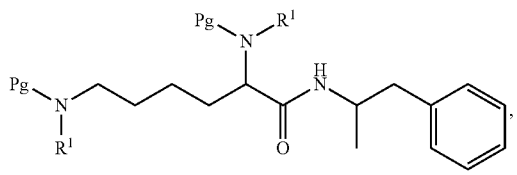

wherein:

Pg represents independently for each occurrence —C($R^2$)$_2$-aryl or —C(O)OC($R^2$)$_2$-aryl;

$R^1$ represents independently for each occurrence hydrogen or $C_1$-$C_6$ alkyl; and $R^2$ represents independently for each occurrence hydrogen or $C_1$-$C_4$ alkyl.

In certain embodiments, Pg is —C(O)OCH$_2$-phenyl, wherein said phenyl is optionally substituted with 1, 2, or 3 substituents independently selected from the group consisting of halogen, $C_1$-$C_6$ alkyl, and $C_1$-$C_6$ alkoxy. In certain other embodiments, Pg is —C(O)OCH$_2$-phenyl.

In certain embodiments, said compound of Formula III is represented by:

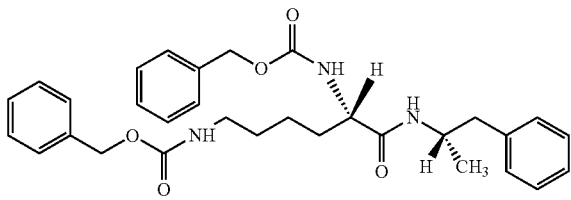 [SMILES: C[C@@H](Cc1ccccc1)NC(=O)[C@H](CCCCNC(=O)OCc1ccccc1)NC(=O)OCc1ccccc1]

In certain embodiments, said compound of Formula III has a purity of at least 99.9% (w/w). In certain embodiments, said compound of Formula III has a purity of at least 99.99% (w/w). In certain embodiments, said compound of Formula III is in the form of a crystalline solid, and optionally further characterized as meeting at least one of the foregoing purity thresholds.

IV. Compound Salt Forms and Pharmaceutical Compositions

Salts forms of the compounds described herein are contemplated. For example, compounds that contain a basic functional group, such as amino or alkylamino, may be capable of forming a salt when admixed with a suitable acid. Preferably, the salt forms relatively non-toxic, inorganic or organic acid addition salts of compounds described herein. These salts can be prepared by reacting a compound described herein in its free base form with a suitable organic or inorganic acid, and isolating the salt thus formed during subsequent purification. Representative salts include the methanesulfonate, trifluoromethanesulfonate, toluenesulfonic, oxalic, ascorbic, hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, glucoheptonate, lactobionate, and laurylsulphonate salts and the like. (See, for example, Berge et al. (1977) "Pharmaceutical Salts", J. Pharm. Sci. 66:1-19)

In other cases, a compound described herein may contain one or more acidic functional groups and, thus, are capable of forming a salt with a base. These salts can be prepared by reacting a compound described herein in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Lisdexamfetamine, related compounds, and salts thereof can be formulated in a pharmaceutical composition. Pharmaceutical compositions comprise a therapeutically-effective amount of one or more of the compounds described above, formulated together with one or more pharmaceutically acceptable carriers (additives) and/or diluents. The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

V. Definitions

To facilitate an understanding of the invention, a number of terms and phrases are defined below.

The term "alkyl" is art-recognized and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 10 or fewer carbon atoms in its backbone (e.g., $C_1$-$C_{10}$ for straight chain, $C_3$-$C_{10}$ for branched chain), and alternatively, about 5 or fewer. Likewise, cycloalkyls have from about 3 to about 10 carbon atoms in their ring structure, and alternatively about 5, 6 or 7 carbons in the ring structure. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "aralkyl" refers to an alkyl group substituted with an aryl group.

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "alkoxy" as used herein refers to an alkyl group attached to an oxygen (—O-alkyl). Exemplary alkoxy groups include, but are not limited to, groups with an alkyl group of 1-12, 1-8, or 1-6 carbon atoms, referred to herein as $C_1$-$C_{12}$alkoxy, $C_1$-$C_8$alkoxy, and $C_1$-$C_6$alkoxy, respectively. Exemplary alkoxy groups include, but are not limited to methoxy, ethoxy, propoxy, butoxy, etc.

The term "aryl" is art-recognized and refers to a carbocyclic aromatic group. Representative aryl groups include phenyl, naphthyl, anthracenyl, and the like. The aromatic ring is optionally substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. The term "aryl" also includes polycyclic ring systems having two or more carbocyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. In certain embodiments, the aromatic ring is not substituted, i.e., an unsubstituted aryl.

The "heteroaryl" is art-recognized and refers to aromatic groups that include at least one ring heteroatom. In certain instances, a heteroaryl group contains 1, 2, 3, or 4 ring heteroatoms. Representative examples of heteroaryl groups includes pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. The heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. The term "haloheteroaryl" refers to an heteroaryl group that is substituted with at least one halogen.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

As used herein, the term "heterocyclic" represents, for example, an aromatic or nonaromatic ring containing one or more heteroatoms. The heteroatoms can be the same or different from each other. Examples of heteratoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like.

The terms "amine" and "amino" are art-recognized and refer to both unsubstituted and substituted amines, e.g., a moiety that may be represented by the general formulas:

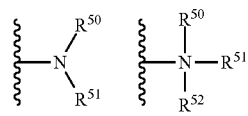

wherein $R^{50}$, $R^{51}$ and $R^{52}$ each independently represent a hydrogen, an alkyl, an alkenyl, —$(CH_2)_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —$(CH_2)_m$—$R^{61}$. Thus, the term "alkylamine" includes an amine group, as defined above, having a substituted or unsubstituted alkyl attached thereto, i.e., at least one of $R^{50}$ and $R^{51}$ is an alkyl group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—$R^{61}$, where m and $R^{61}$ are described above.

The symbols "*" and " ⌇ " used in certain chemical structures indicates the point of attachment of the chemical fragment.

The term "manufacturing scale" refers to a chemical process carried out using at least 30 kg of a reacting agent (e.g., at least 30 kg of D-amphetamine is reacted with the necessary amount of said compound of Formula II; See Example 1), or at least about 40 kg, 60 kg, 80 kg, or 100 kg of a reacting agent.

The term "hydrogen source" refers to a composition capable of providing hydrogen during a chemical reduction reaction. Exemplary hydrogen sources include hydrogen gas and ammonium formate.

Certain compounds described herein may exist in particular geometric or stereoisomeric forms. The invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. For generic chemical structures presented herein, the generic chemical structure is meant to encompass cis- and trans-isomers, a R-enantiomer, a S-enantiomer, diastereomers, and/or mixtures thereof unless the chemical structure or associated definition(s) species otherwise.

If, for instance, a particular enantiomer of compound of the invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

Pharmaceutically acceptable salts of the compounds described herein are contemplated. As used herein, the term "pharmaceutically acceptable salt" refers to any pharmaceutically acceptable salt (e.g., acid or base) of a compound described herein which, upon administration to a subject, is capable of providing a compound of this invention or an active metabolite or residue thereof. As is known to those of skill in the art, "salts" of the compounds described herein may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the invention compounded with a suitable cation such as Na$^+$, NH$_4^+$, and NW$_4^+$ (wherein W is a $C_{1-4}$ alkyl group), and the like.

As a general matter, compositions specifying a percentage are by weight unless otherwise specified. Further, if a variable is not accompanied by a definition, then the previous definition of the variable controls.

EXAMPLES

The invention now being generally described, will be more readily understood by reference to the following examples, which are included merely for purposes of illustration of certain aspects and embodiments of the invention, and are not intended to limit the invention.

Example 1

Preparation of N,N'-Biscarbobenzyloxy-Lisdexamfetamine (LDX-(Cbz)$_2$)

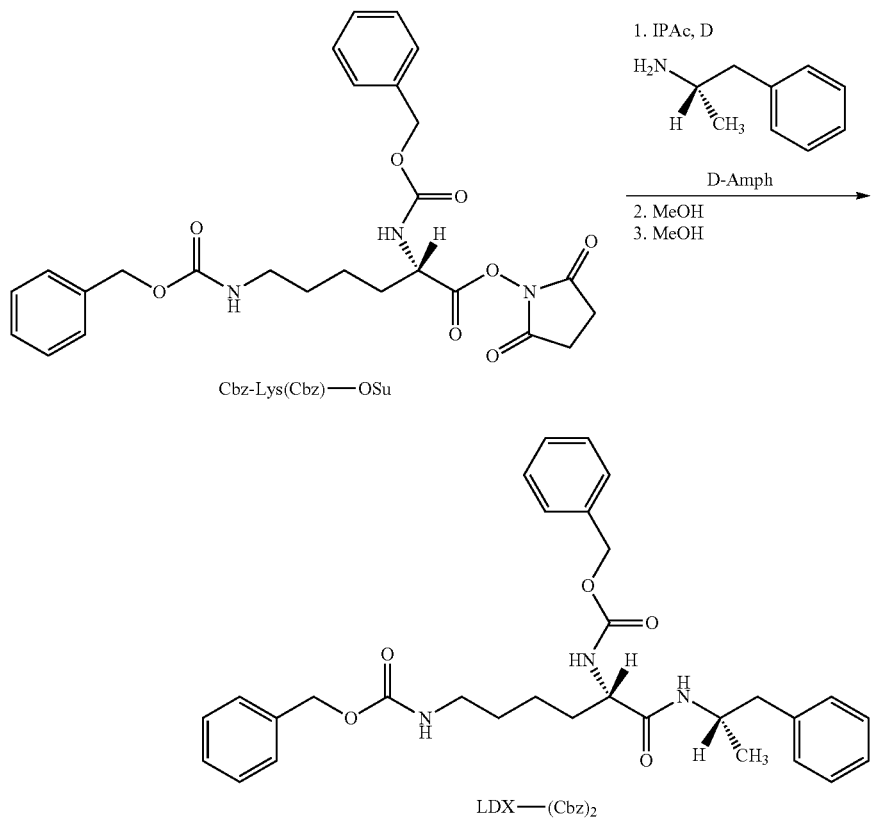

General Experimental Procedure: In an appropriately sized, inert jacketed reactor charge 378.3 g of Cbz-Lys(Cbz)-OSu and 2309 g of isopropyl acetate. Heat the stirred slurry to ~50° C. In a second reactor mix 100.0 g of D-amphetamine into 165 g of isopropyl acetate. Add the D-amphetamine solution to the batch over 1.75-2.25 hours. After the addition is complete stir the heterogeneous mixture at 50-55° C. until the reaction is complete by HPLC analysis. Charge 1197 g of methanol and heat the batch at a vigorous reflux 1 hour. Cool the batch to 45-55° C. over 2 hours then hold at temperature for 14-16 hours. Cool the batch to 15-25° C. at a rate of 5-10° C. per hour. Filter the slurry. Rinse the wet cake with 449 g of methanol and dry on the filter under nitrogen. To a clean, dry reactor charge the crude solids and 1642 g of methanol. Stir the slurry and heat to a vigorous reflux for 2 hours. Cool the batch to 45-55° C. over 1-2 hours then hold at temperature 12-16 hours. Continue cooling to 15-25° C. at a rate of 5-10° C. per hour. Filter the slurry and wash the wet cake with 547 g of methanol. Vacuum dry the wet cake at ~55° C. to give product as a white to off-white solid (332 g, 88 mol %).

The crude LDX-(Cbz)$_2$ product isolated from the reaction mixture by crystallization had a purity of 99.96% according to HPLC analysis. $^1$H NMR analysis of crude LDX-(Cbz)$_2$ product revealed the presence of 0.57% by weight N-hydroxysuccinimide. The purified LDX-(Cbz)$_2$ product obtained by re-crystallization from methanol had a purity of 99.99% according to HPLC analysis. $^1$H NMR analysis of the purified LDX-(Cbz)$_2$ product obtained by re-crystallization from methanol revealed that the amount of N-hydroxysuccinimide in the purified LDX-(Cbz)$_2$ product was reduced to 0.05% by weight.

Example 2

Preparation of Lisdexamfetamine Dimesylate

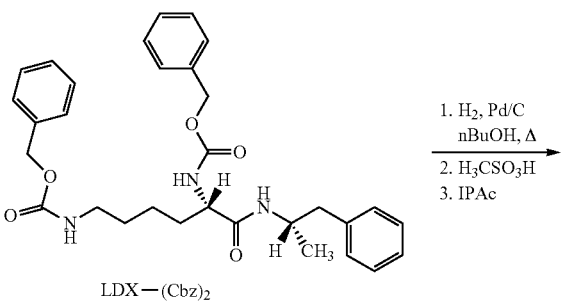

-continued

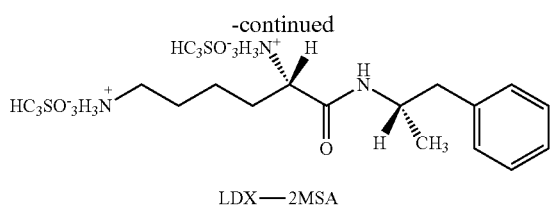

LDX—2MSA

General Experimental Procedure: In an appropriately sized, inert autoclave charge 100.0 g of LDX-(Cbz)$_2$, 1 g of 10% (50% wet) palladium on carbon and 607.5 g of n-butanol. Stir the mixture under 100-150 psi of hydrogen at 80-85° C. until the reaction is complete by HPLC analysis. Heat the batch to 95-97° C. and hot filter. Transfer the product rich filtrate to an appropriately sized glass reactor. Charge 7.6 g of methanesulfonic acid maintaining a batch temperature of 32-38° C. To the resulting solution add 1.3 g of LDX-2MSA seed crystal. Stir the batch 4-16 hours at 32-38° C. Charge 30.4 g of methanesulfonic acid to the slurry over not less than 2 hours maintaining a batch temperature of 32-38° C. After the addition stir 1-2 hours at 32-38° C. Charge 436 g of isopropyl acetate over not less than 2 hours, then stir 1-2 hours at 32-38° C. Cool the batch to 15-25° C. and hold 1 hour. Filter the slurry. Wash the wet cake with a premixed combination of n-butanol (91.5 g) and isopropyl acetate (32.7 g) followed by a wash of isopropyl acetate (87.2 g). Vacuum dry the wet cake at ~50° C. to give product as a white to off-white solid (78.8 g, 92 mol %).

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A method of preparing a lysine-amphetamine compound, comprising admixing an amphetamine compound of Formula I with a lysine compound of Formula II to provide a lysine-amphetamine compound of Formula III, wherein Formula I is represented by:

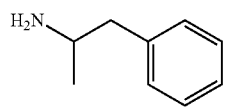

or a salt thereof;

Formula II is represented by:

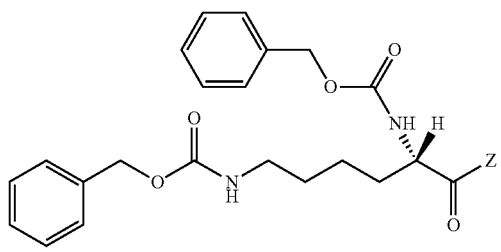

wherein Z is

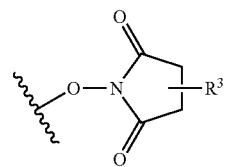

and R$^3$ is hydrogen; and
Formula III is represented by:

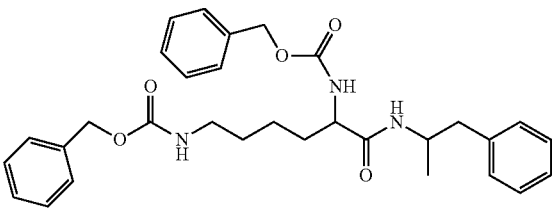 [SMILES: CC(Cc1ccccc1)NC(=O)C(CCCCNC(=O)OCc1ccccc1)NC(=O)OCc1ccccc1]

and crystallizing said lysine-amphetamine compound of Formula III from a mixture comprising (i) at least one of a C$_1$-C$_4$ aliphatic alcohol, C$_1$-C$_4$ aliphatic carboxylic acid, aliphatic tertiary amine, or water, and (ii) (C$_1$-C$_4$ alkyl)—CO$_2$—(C$_1$-C$_4$ alkyl), to provide a purified lysine-amphetamine compound of Formula III.

2. The method of claim 1, wherein Formula I is

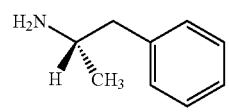

having a purity of at least 90% (w/w), Formula II is

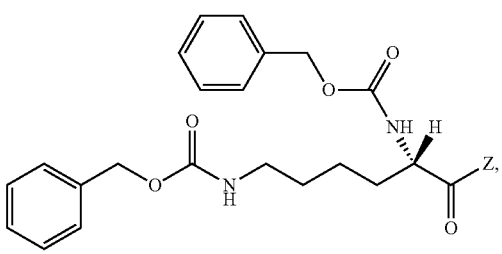

and Formula III is

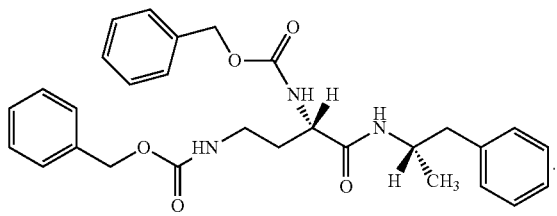 [SMILES: C[C@@H](Cc1ccccc1)NC(=O)[C@H](CCNC(=O)OCc1ccccc1)NC(=O)OCc1ccccc1]

3. The method of claim 1, wherein Formula I has a purity of at least 97% (w/w).

4. The method of claim 1, comprising crystallizing said lysine-amphetamine compound of Formula III from a mixture comprising (i) at least 20% (v/v) methanol, and (ii) at least 20% (v/v) isopropyl acetate, to provide a purified lysine-amphetamine compound of Formula III.

5. The method of claim 1, comprising re-crystallizing said purified lysine-amphetamine compound of Formula III from a mixture comprising at least one of a $C_1$-$C_4$ aliphatic alcohol, $C_1$-$C_4$ aliphatic carboxylic acid, aliphatic tertiary amine, or water, to provide a high-purity lysine-amphetamine compound of Formula III.

6. The method of claim 1, wherein the purified lysine-amphetamine compound of Formula III has a purity of at least 99% (w/w).

7. The method of claim 5, wherein the high-purity lysine-amphetamine compound of Formula III has a purity of at least 99.9% (w/w).

8. The method of claim 1, further comprising admixing said lysine-amphetamine compound of Formula II, a hydrogenation catalyst, and a hydrogen source to provide a lysine-amphetamine compound of Formula IV, wherein the compound of Formula IV is represented by:

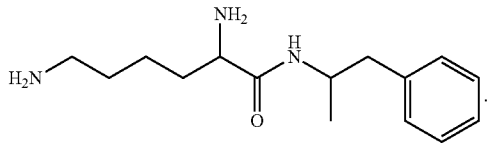 [SMILES: CC(Cc1ccccc1)NC(=O)C(N)CCCCN]

9. The method of claim 8, wherein the hydrogenation catalyst comprises palladium on carbon, and the hydrogen source is hydrogen gas or ammonium formate.

10. The method of claim 8, further comprising admixing said lysine-amphetamine compound of Formula IV and an acid to provide an acid salt of said lysine-amphetamine compound of Formula IV.

11. The method of claim 10, wherein the acid is methanesulfonic acid.

12. The method of claim 10, further comprising admixing a lysine compound of Formula V with a carboxylic acid-activating agent to provide a lysine compound of Formula II; wherein the lysine compound of Formula V is represented by:

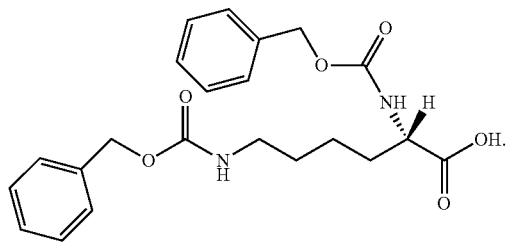 [SMILES: O=C(NCCCC[C@H](NC(=O)OCc1ccccc1)C(=O)O)OCc1ccccc1]

13. The method of claim 1, wherein the purified lysine-amphetamine compound of Formula III contains less than 0.6% (w/w) N-hydroxysuccinimide.

14. The method of claim 1 wherein the admixing of the amphetamine compound of Formula I with the lysine compound of Formula II to provide the lysine-amphetamine compound of Formula III is done with no additional base.

15. The method of claim 14 wherein the admixing of the amphetamine compound of Formula I with the lysine compound of Formula II to provide the lysine-amphetamine compound of Formula III is done with no diisopropylethylamine.

* * * * *